United States Patent [19]

Martenson

[11] Patent Number: 5,452,725
[45] Date of Patent: Sep. 26, 1995

[54] CABLE TERMINATION STATUS DETECTION

[75] Inventor: John E. Martenson, Auckland, New Zealand

[73] Assignee: Fisher & Paykel Limited, Auckland, New Zealand

[21] Appl. No.: 23,572

[22] Filed: Feb. 26, 1993

[30] Foreign Application Priority Data

Feb. 27, 1992 [NZ] New Zealand .............................. 241754

[51] Int. Cl.⁶ .................................................. A61B 17/36
[52] U.S. Cl. ................................ 128/736; 600/22; 606/35
[58] Field of Search ...................:........................ 128/736, 630, 128/639, 696, 908; 600/21, 211; 606/35; 324/532–535

[56] References Cited

U.S. PATENT DOCUMENTS 4,498,479  2/1985  Martio et al. ............................ 128/696

FOREIGN PATENT DOCUMENTS 2913048  10/1980  Germany ............................... 128/639

OTHER PUBLICATIONS

Halverson et al; "Transmission Line Testing Using the Sampling Oscilliscope" All pages; 15 Mar. 1962.

Primary Examiner—William E. Kamm
Assistant Examiner—Marianne Parker
Attorney, Agent, or Firm—Trexler, Bushnell, Giangiorgi & Blackstone, Ltd.

[57] ABSTRACT

A method and apparatus for detection of the status of a cable termination. The cable is required to be terminated by being in contact with the body of a patient in a medical environment. The apparatus warns a user if the cable is disconnected from the patient. The status of the termination is established by applying a pulse of electrical energy to the cable and detecting the reflections produced in response to application of the pulse. A characteristic of the reflections is detected and compared with a predetermined characteristic to determine whether the cable is connected to the patient.

12 Claims, 2 Drawing Sheets

CABLE TERMINATION STATUS DETECTION

BACKGROUND OF THE INVENTION (1) Field of the Invention

This invention relates to methods of and/or apparatus for detecting the status of a cable termination and has been devised particularly but not solely for use in detecting the status of the connection between a patient and one or more cables from a patient monitoring system such as those monitoring systems used in the healthcare industry.

(2) Description

In medical patient monitoring systems requiring attachment of electrical cables to the body of a patent, it can be of considerable advantage to know if such cables are correctly terminated. A detached cable may not be immediately obvious resulting in time wasting fault diagnosis or a possible life threatening situation. For example, careful control of a physical characteristic such as body temperature is often required for patients such as new-born babies (infants) in hospital environments. Once such way of controlling an infant's body temperature is to place the infant in a warmer. The warmer maintains the body temperature of an infant and radiates heat selectively when or as required to maintain the body temperature of the infant at a desired level. The infant's body temperature is measured by the warmer control circuitry using an electric cable having a temperature probe attached to an external surface of the infants body.

It is important that the cable is correctly terminated, that is, that the temperature probe is in secure contact with the infant's body in order that an accurate measurement of the infant's body temperature may be made. It would clearly be advantageous if the warmer control sound an audible alarm or show a visible alarm if the temperature probe was not securely connected to the infants body. This is especially important since at present a visual inspection is used to determine if a cable is connected to a patient and this is not always sufficient for the user to determine whether the probe is in fact securely connected.

BRIEF SUMMARY OF THE INVENTION

It is an object of the present invention to provide methods of and/or apparatus for detecting the status of a cable termination which will at least go some way toward overcoming the above disadvantages or which will at least provide the public with a useful choice.

Accordingly, in one aspect, the invention consists in temperature measuring apparatus for measuring a patient's body temperature in a medical environment including a temperature probe having a temperature sensor. The apparatus also including an electric cable containing conductors and having a proximal end and a distal end to which the temperature probe is attached. The temperature probe in use being attached to the patient. An electrically conductive portion of the temperature sensor is adapted to be placed on the patient's body and is in electrical connection with a conductor in the electric cable. There existing a thermal connection of a measurable quality between the temperature sensor and the patient, and means for determining the quality of the thermal connection. The means for determining the quality of the thermal connection comprising pulse generating means having an output connected at the proximal end of the electric cable for generating a pulse of electrical energy on the electric cable which is propagated along the electric cable towards a load comprising the patient in thermal contact with the temperature probe. Some of the energy of the pulse being reflected by the load as reflected propagating electrical waves having at least one physical characteristic between the proximal and distal ends of the electric cable and some of the energy being absorbed by the load. Signal detection means for detecting the at least one physical characteristic of the reflected propagating electrical waves in response to the pulse are also provided. The reflected propagating electrical waves having a measurable duration and amplitude. The temperature sensor providing a signal indicative of the patient's body temperature to the conductor in the electric cable. Comparing means compare the at least one physical characteristic of the reflected propagating electrical waves with a predetermined signal characteristic to thereby provide an indication of the quality of the thermal connection.

In a second aspect the invention consists in a method of measuring a patient's body temperature in a medical environment with a temperature probe having a temperature probe in use attached to the patient. An electric cable is provided having a proximal end and a distal end to which the temperature probe is attached. There existing a thermal connection of a measurable quality between the temperature sensor and the patient. The method also including detecting the quality of the thermal connection, the method comprising the steps of periodically generating a pulse of electrical energy and applying the pulse to the proximal end the electric cable. Then detecting a characteristic of reflections resulting from the pulse interacting with a load, comprising the patient in thermal connection with the temperature probe, and the proximal end of the electric cable, the reflections having a measurable duration and amplitude. The providing the distal end of the cable with a signal indicative of the temperature sensed by the temperature sensor. Finally comparing the characteristic with a predetermined signal characteristic to determine the quality of the thermal connection.

The invention consists in the foregoing and also envisages constructions of which the following gives examples only.

DETAILED DESCRIPTION

Figure 1:
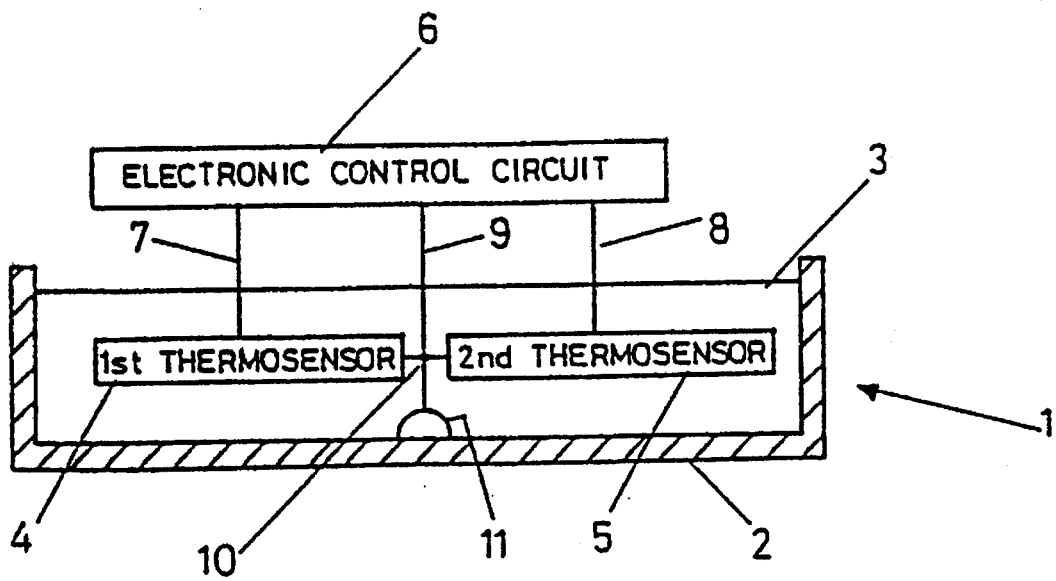
FIGS. 1 and 2 are diagrammatic elevational views of a section through a probe for use with the present invention.

Referring to FIG. 1 a temperature probe is shown generally referenced 1 having a cup constructed from an electrically conductive material such as metal and having a thermally conductive paste 3 therein in which one or more temperature sensors are disposed. The first and second thermosensors 4 and 5 are electrically connected to electronic control circuitry generally referenced 6 by a cable having conductors 7 and 8 and a common conductor 9. The thermosensors are connected to common conductor 9 at point 10 and this common connection is also electrically connected to the metal cup 2 by soldering or clamping for example at point 11.

Figure 2:
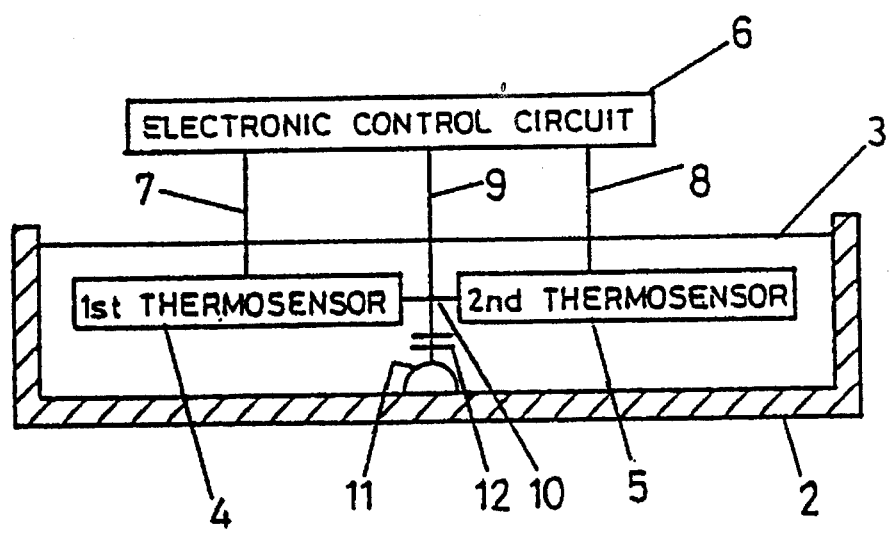

Referring to FIG. 2, the probe cup of FIG. 1 is again shown only in this probe the connection between the common conductor at point 10 and the metal cup at point 11 is made through a capacitor referenced 12.

Figure 3:
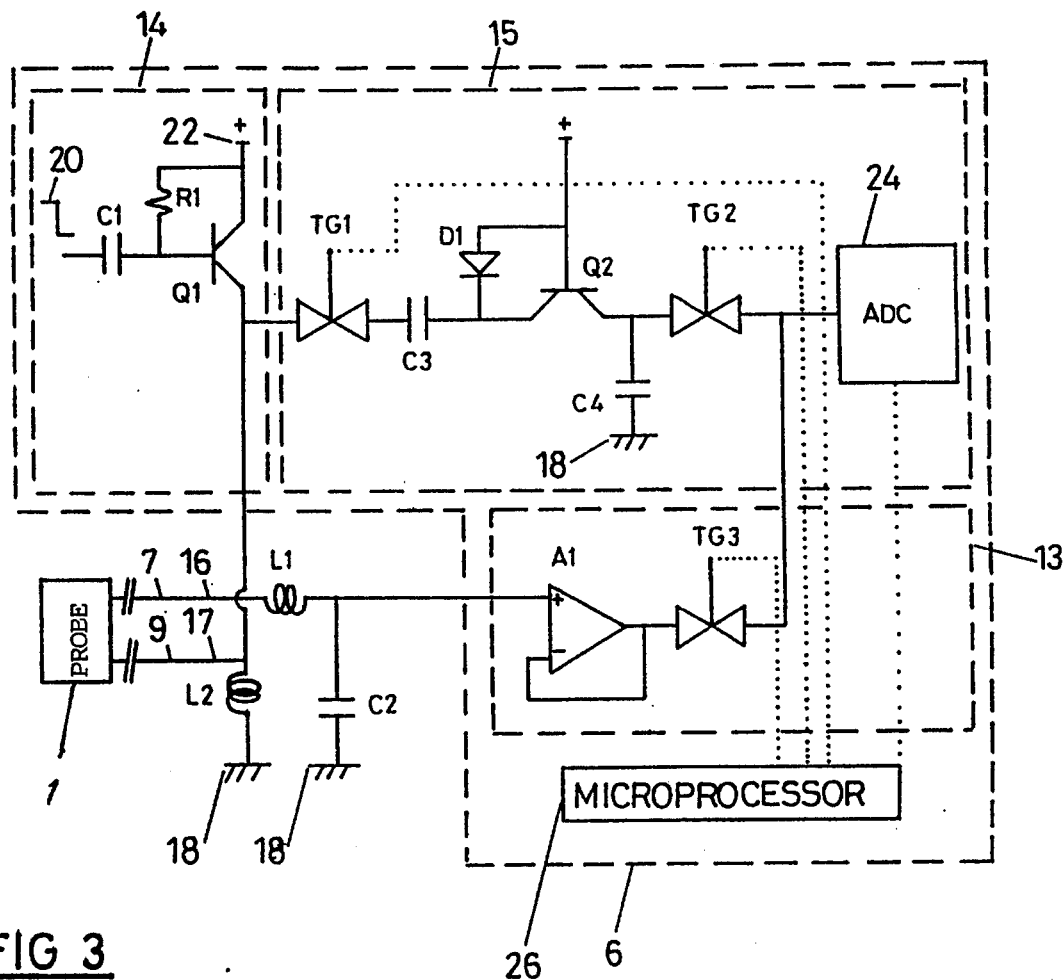
FIG. 3 is a simplified circuit diagram of the apparatus used in accordance with the present invention.

Referring to FIG. 3 a probe 1 is shown at the distal end of a cable and in the figure the common conductor 9 of the cable is shown together with one of the conductors 7 or 8 or both conductors. For simplicity, only conductors 7 and 9 are shown in FIG. 3. At the proximal end of the cable the electronic control circuitry 6 is generally shown within a box having a dashed border. The control circuitry 6 comprises four main sections, being temperature measuring circuitry 13, pulse generating circuitry 14, signal detection circuitry 15 and microprocessor 26 for overall circuit control. Also, connected between the cable terminals 16 and 17 at the proximal end of the cable and the electronic circuitry 6 is capacitor C2 and inductors L1 and L2. The electronic circuitry 6 has a common reference potential 18.

The temperature measuring circuitry 13 comprises an operational amplifier A1 configured to provide a gain of unity (that is to act as a buffer) having the non-inverting input connected to inductor L1 and capacitor C2 and having the output connected to transmission gate TG3. Transmission gate TG3 is also connected to Analog to Digital converter 24.

The pulse generating circuitry 14 comprises capacitor C1 which is connected between the base of the transistor Q1 and apparatus for producing a transient signal or level shift 20. The emitter of Q1 is connected to the positive or high-potential rail of power supply 22. The reference or low-potential rail of the power supply is connected to a ground rail 18. Connected between the emitter and base of transistor Q1 is resistor R1 and the collector of Q1 is connected to terminal 17 (conductor 9 of the cable).

The signal detection circuitry 15 comprises a transmission gate TG1 between terminal 17 and one side of the capacitor C3. The other side of the capacitor C3 is connected to the emitter of transistor Q2. The base of transistor Q2 is connected to positive rail 22 of a D.C. power supply and diode D1 is connected between the base and emitter of Q2. The collector of Q2 is connected to transmission gate TG2 and the capacitor C4 is connected between the collector of Q2 and the ground rail 18. Transmission gate TG2 is also connected to an analog to digital converter 24.

If the individual conductors of the cable, connected to a probe which is to be in direct contact with the body, for example the abdomen of the patient, are considered lumped together as shown in FIG. 3, and a voltage pulse is applied at the end remote from the patient (the proximal end), a voltage wave will propagate the length of the cable. On reaching the distal end of the cable this voltage will, in the case of a correctly terminated cable (connected to a patient), be largely dissipated in the principally resistive patient load. However, if the probe cable is unattached at the distal end, this voltage will be substantially reflected back along the cable to the transmitting end. The status or condition of the distal cable end, as to whether it is terminated correctly on the patient or not can be determined by measuring the form of this reflected voltage signal.

Figure 4:
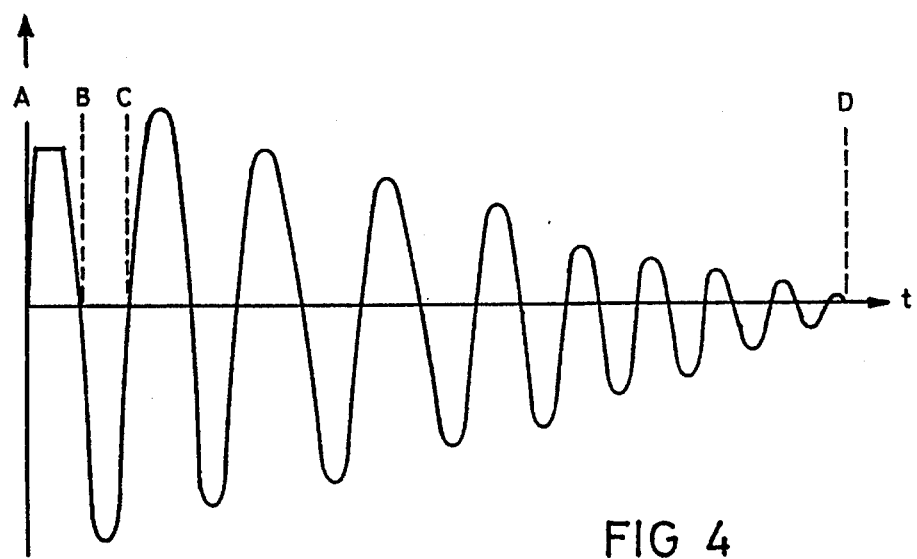
FIG. 4 is a graph of amplitude vs time for a waveform produced by the circuitry shown in FIG. 3.

In a practical application of this principle a cable termination status detection circuit is connected to a patient temperature measuring probe installation for example, in which the probe of FIGS. 1 or 2 is connected to the abdomen of a patient, being held in place by a reflective dot which has an adhesive surface to ensure the probe is held in place on the skin of the patient. To generate the pulse or pulses required to establish the status of the cable termination, that is the probe connection to a patient, the transient signal represented by wave form 20 is applied and passed through C1 to base of Q1. Conduction between the emitter and collector of Q1 then occurs while C1 discharges through R1. This gives a short pulse of current across inductor L2, that is between the cable and the ground rail 18. Referring to FIG. 4 the conduction period of Q1 is indicated by period A–B. The applied pulse voltage of period A-B is propagated through the cable to its distal end and some reflection will occur so that reflections will oscillate through the cable at the self resonant frequency of the cable. The ringing oscillation persists for a finite time after the initial exciting voltage pulse has ended.

The oscillation is caused by the voltage signal propagating along the length of the cable and reflecting from the loads at the terminations or ends of the cable. Thus a cable which is in electrical connection with a probe or transducer which is not in contact with the body of a patient will have no load connected to the probe or transducer (the termination) in which the pulse may be dissipated, and the voltage pulse propagating along the length of the cable will be reflected back toward the pulse generating circuitry where it will again be reflected back toward the termination. This oscillation will continue until the losses in the cable and associated components dissipate the energy supplied by the initial pulse.

When the probe is in contact with a patient, as required for accurate temperature measurement by the temperature measuring circuitry, the voltage pulse, after propagating along the length of the cable will be largely dissipated in the body of the patient which comprises a resistive load. The voltage pulse travels through the cable conductors 7, 8 and 9, and onto the probe cup 2 through connection 11, and capacitor 12 if it is present, and into the body of the patient. The cable conductors 7, 8 and 9 may be considered lumped together as a single conductor, at the signal frequencies used to test the termination status since they are located adjacent to each other and are capacitively coupled to each other. The reflected signal from the load comprising the patient is minimal since most of the energy of the initial pulse is dissipated in the load, and the oscillation along the cable is therefore reduced considerably compared with the oscillation present when there is a no load condition at the cable termination. The amplitude, duration and shape of the oscillation will vary depending on factors such as the length of the cable and the amplitude, duration, shape and frequency of the initial pulse. Thus if a standard length of cable is supplied and the initial voltage pulse is of a constant, known form, then no calibration of the detection circuitry is necessary.

L1 and C2 form a low pass filter which confines the temperature probe cable oscillations and inhibit their entry into the temperature measurement circuit amplifier A1. Interference from the probe cable oscillations is not of great concern as the temperature measurement phase is distinct from the determination of the status of the probe cable termination. That is, because it takes very little time to determine the status of the probe termination in accordance with the present invention, regular checks upon the status of the cable termination may be made (once every second for example) and the time between status checks may be used to provide indications from the thermosensors to amplifier A1 for providing indications for temperature measurement.

After the reverse voltage spike referenced B–C in FIG. 4, the inductor L2, probe cable 7 and 9 and sensor 1 are oscillating at their natural resonant frequency. At point C, transmission gate TG1 is closed and the diode-transistor pump circuit of C3, D1, Q2 and C4 sums the remaining oscillations referenced C–D in FIG. 4. Each transmission gate delivers an output waveform that is a replica of that input to the gate. Each transmission gate is activated by microprocessor 26. The cable oscillations are provided to C3 by TU1 and pass through C3 to the emitter of Q2 which is maintained at a potential of approximately 0.6 volts below rail 22 by D1. The cable oscillations are summed by charge storage in capacitor C4. Each positive oscillation above a predetermined threshold amplitude corresponding to approximately 0.6 volts will forward bias Q2 and current will be supplied to C4. Thus characteristics of the reflected signal indicating its amplitude and duration are detected and these are summed cumulatively. The circuit may be modified to sum one or both of these characteristics. At point D the transmission gate TG1 is opened and TG2 is closed. The voltage across capacitor C4 is then read by the analog to digital converter 24 to provide an indication of the magnitude of the voltage across C4 in digital form. The typical time between points A and D in FIG. 4 is usually 3 to 5 microseconds for example.

The oscillations C–D represent an un-terminated temperature probe. Therefore when the probe is correctly attached to the patient, the oscillations are reduced in amplitude and number, resulting in a lower voltage across capacitor C4. When the value of the voltage across capacitor C4 is represented in binary form by analog to digital converter 24, the resultant binary representation of the voltage will be much lower and this can be compared with the threshold value corresponding to a predetermined signal characteristic or combination thereof relating to the minimum duration and/or amplitude of the reflected signal. The threshold value is stored in software associated with or included in microprocessor 26 which controls the circuitry described above.

The micro-processor controls the circuitry described to sequentially switch, under software control, the transmission gates TG1 to TG3 and process the result provided by A to D converter 24 to indicate an unterminated probe cable by audible and/or visual alarms.

The signals indicative of the temperature of the patient are passed from thermo-sensor 4 through cable 7 to buffer A1. When temperature is required to be measured by the control circuitry, gate TG1 is opened and gate TG3 is closed so that the A to D converter converts analog signals representative of the temperature of the patient and presents these to the micro-processor control circuitry in binary form for control of the heat, for example, being supplied to the patient.

The advantages of this method of determining correct probe attachment to a patient, are that the function can be completed within a time span of the order of 5 micro seconds and thus can be slotted into a regular temperature measuring routine with minimal or no interference. Also the function need only be repeated at a frequency which will give adequate warning. Once a second is sufficient and the above function can be completed with less than 20 nanowatts of dissipated power.

The temperature measuring circuit in which the generating and detection circuitry is installed is totally isolated from ground leakage, that is, the probe is double insulated and is supplied by a dedicated high frequency switching power supply. This isolation from ground does not affect the operation of the generating and detection circuitry.

We claim:

1. Temperature measuring apparatus for measuring a patient's body temperature in a medical environment including a temperature probe having a temperature sensor an electric cable containing conductors and having a proximal end and a distal end to which said temperature probe is connected, an electrically conductive portion of said temperature sensor adapted to be placed on said patient's body and being in electrical connection with a conductor in said electric cable, said temperature sensor providing a signal indicative of said patient's body temperature to said conductor in said electric cable, there existing a thermal connection of a measurable quality between said temperature sensor and said patient, and means for determining said quality of said thermal connection, said means comprising:

pulse generating means having an output connected at said proximal end of said electric cable for generating a pulse of electrical energy on said electric cable which is propagated along said electric cable towards a load in thermal contact with said temperature probe, some of said energy of said pulse being reflected by said load as reflected propagating electrical waves having at least one physical characteristic between said proximal and distal ends of said electric cable and some of said energy being absorbed by said load, signal detection means for detecting said at least one physical characteristic of said reflected propagating electrical waves in response to said pulse, said reflected propagating electrical waves having a measurable duration and amplitude, and comparing means to compare said at least one physical characteristic of said reflected propagating electrical waves with a predetermined signal characteristic to thereby provide an indication of the quality of said thermal connection.

2. Temperature measuring apparatus as claimed in claim 1 wherein said at least one physical characteristic comprises an indication of said duration of said reflected propagating electrical waves.

3. Temperature measuring apparatus as claimed in claim 1 wherein said at least one physical characteristic comprises an indication of said amplitude of said reflected propagating electrical waves.

4. Temperature measuring apparatus as claimed in claim 1 wherein said signal detection means comprise summing means which detect said at least one physical characteristic by accumulating an indication of the energy of said reflected propagating electrical waves until said amplitude of said reflected propagating electrical waves is less than a predetermined threshold amplitude.

5. Temperature measuring apparatus as claimed in claim 4 wherein said summing means also cumulatively sum an indicator of both said amplitude and said duration of said reflected propagating electrical waves.

6. Temperature measuring apparatus as claimed in claim 5 wherein said predetermined signal characteristic has a known magnitude and said comparing; means compare said predetermined signal characteristic with said summation and indicate that said temperature sensor is disconnected from said patient if said summation is greater than said predetermined signal characteristic.

7. Temperature measuring apparatus as claimed in claim 6 wherein said signal detection means comprise energy storage means and signal value conversion means, said energy storage means storing energy from said reflected propagating electrical waves for input to said signal value conversion means and said signal value conversion means determining and outputting a numerical value representing the magnitude of signals input thereto and wherein control means control said signal detection means and the state of at least two transmission gate means for transmitting and blocking electrical signals, at least one of said at least two transmission gate means connected between said temperature probe and said energy storage means and at least one of said at least two transmission gate means connected between said temperature probe and said signal value conversion means, and wherein said control means selectively open only one of said at least two transmission gate means at one time to exclusively allow said signal value conversion means to output a value representing either said patient's body temperature or the quality of said thermal connection.

8. A method of measuring a patient's body temperature in a medical environment with a temperature probe having a temperature probe in use connected to said patient, an electric cable having a proximal end and a distal end to which said temperature probe is attached, there existing a thermal connection of a measurable quality between said temperature sensor and said patient and detecting the quality of said thermal connection said method comprising the steps of periodical generating a pulse of electrical energy and applying said pulse to the proximal end of said electric cable, detecting a characteristic of reflections resulting from said pulse interacting with a-load, in thermal connection with said temperature probe, and said proximal end of said electric cable, said reflections having a measurable duration and amplitude, providing the distal end of said cable with a signal indicative of the temperature sensed by said temperature sensor, and comparing said characteristic with a predetermined signal characteristic to determine the quality of said thermal connection.

9. A method as claimed in claim 8 wherein said step of detecting said signal characteristic comprises the step of summing an indication of said duration of said reflections until said amplitude is below a predetermined threshold amplitude.

10. A method as claimed in claim 9 including the step of cumulatively summing an indication of both said amplitude and said duration of said reflections.

11. A method as claimed in claim 10 wherein said predetermined signal characteristic has a known magnitude and including the step of comparing said predetermined signal characteristic with said summation and indicating the quality of said thermal connection is poor if said summation is greater than said predetermined signal characteristic.

12. A method as claimed in claim 11 including the step of switching said electric cable between detecting the quality of the thermal connection of said probe to said patient and conducting said indication of the temperature sensed by said temperature sensor.

* * * * *